(12) United States Patent
Mautner et al.

(10) Patent No.: US 11,357,530 B2
(45) Date of Patent: Jun. 14, 2022

(54) SYSTEMS AND METHODS FOR TISSUE TREATMENT

(71) Applicant: Emory University, Atlanta, GA (US)

(72) Inventors: Kenneth R. Mautner, Atlanta, GA (US); Luka Grujic, Boston, MA (US); Shawna M. Hagen, Atlanta, GA (US); Brett Rogers, Macon, GA (US); Jonathan Shaw, Atlanta, GA (US)

(73) Assignee: Emory University, Atlanta, GA (US)

( * ) Notice: Subject to any disclaimer, the term of this patent is extended or adjusted under 35 U.S.C. 154(b) by 267 days.

(21) Appl. No.: 16/826,497

(22) Filed: Mar. 23, 2020

(65) Prior Publication Data

US 2020/0214732 A1 Jul. 9, 2020

Related U.S. Application Data

(63) Continuation of application No. 15/307,070, filed as application No. PCT/US2015/027909 on Apr. 28, 2015, now Pat. No. 10,631,888.

(Continued)

(51) Int. Cl.
*A61B 17/34* (2006.01)
*A61B 17/32* (2006.01)
(Continued)

(52) U.S. Cl.
CPC .... *A61B 17/32002* (2013.01); *A61B 17/1624* (2013.01); *A61B 17/3478* (2013.01);
(Continued)

(58) Field of Classification Search
CPC ............ A61B 10/0233; A61B 17/1624; A61B 17/32002; A61B 17/3401; A61B 17/3403; A61B 17/3417; A61B 17/3421; A61B 17/3468; A61B 17/3478; A61B 2017/320024; A61B 2017/320028;
(Continued)

(56) References Cited

U.S. PATENT DOCUMENTS 2,705,949 A 4/1955 Silverman
4,020,555 A 5/1977 Hedrick
(Continued)

FOREIGN PATENT DOCUMENTS

DE 102009011970 A1 9/2010

OTHER PUBLICATIONS

International Search Report for International Application No. PCT/US2015/027909, dated Aug. 3, 2015.
(Continued)

*Primary Examiner* — Ryan J. Severson
(74) *Attorney, Agent, or Firm* — Eversheds Sutherland (US) LLP

(57) ABSTRACT

Systems and methods are configured to treat a tissue by automatically linearly oscillating an instrument into a target site. A system may include a body having a length and configured to receive a portion of the instrument guide member having an exposed end and/or an instrument. The system may further include an actuator member disposed within the body and configured to linearly oscillate the instrument within the instrument guide member a fixed distance past the exposed end. The systems and methods can increase patient comfort while empowering clinicians by simplifying interventions for musculoskeletal disorders.

20 Claims, 5 Drawing Sheets

Related U.S. Application Data

(60) Provisional application No. 61/985,012, filed on Apr. 28, 2014.

(51) Int. Cl.
*A61B 17/16* (2006.01)
*A61B 17/00* (2006.01)

(52) U.S. Cl.
CPC . *A61B 17/3421* (2013.01); *A61B 2017/00734* (2013.01); *A61B 2017/320028* (2013.01)

(58) Field of Classification Search
CPC ....... A61B 2017/320032; A61B 2017/320052; A61B 2017/3405; A61B 2017/3409; A61B 2017/347
See application file for complete search history.

(56) References Cited

U.S. PATENT DOCUMENTS

| | | | |
|---|---|---|---|
| 4,489,724 A | 12/1984 | Arnegger |
| 4,644,952 A | 2/1987 | Patipa et al. |
| 4,700,702 A | 10/1987 | Nilsson |
| 4,936,845 A | 6/1990 | Stevens |
| 5,368,045 A | 11/1994 | Clement et al. |
| 5,423,330 A | 6/1995 | Lee |
| 5,833,643 A | 11/1998 | Ross et al. |
| 6,083,244 A | 7/2000 | Lubberts et al. |
| 6,402,701 B1 | 6/2002 | Kaplan et al. |
| 6,689,072 B2 | 2/2004 | Kaplan et al. |
| 6,984,241 B2 | 1/2006 | Lubbers et al. |
| 7,390,330 B2 | 6/2008 | Harp |
| 7,611,521 B2 | 11/2009 | Lubbers et al. |
| 7,662,128 B2 | 2/2010 | Salcudean et al. |
| 7,666,186 B2 | 2/2010 | Harp |
| 7,670,328 B2 | 3/2010 | Miller |
| 7,708,759 B2 | 5/2010 | Lubbers et al. |
| 7,758,518 B2 | 7/2010 | Perez et al. |
| 7,803,123 B2 | 9/2010 | Perez et al. |
| 7,837,687 B2 | 11/2010 | Harp |
| 7,837,700 B2 | 11/2010 | Harp |
| 8,080,011 B2 | 12/2011 | Harp |
| 8,114,129 B2 | 2/2012 | Lubbers et al. |
| 8,137,287 B2 | 3/2012 | Cooke |
| 8,298,253 B2 | 10/2012 | Charles |
| 8,545,502 B2 | 10/2013 | Harp |
| 8,747,426 B2 | 6/2014 | Underwood |
| 2002/0055689 A1 | 5/2002 | Kaplan et al. |
| 2002/0077631 A1 | 6/2002 | Lubbers et al. |
| 2002/0169420 A1 | 11/2002 | Galt et al. |
| 2003/0088270 A1 | 5/2003 | Lubbers et al. |
| 2004/0024420 A1 | 2/2004 | Lubbers et al. |
| 2004/0122459 A1 | 6/2004 | Harp |
| 2004/0133168 A1 | 7/2004 | Salcudean et al. |
| 2004/0162505 A1 | 8/2004 | Kaplan et al. |
| 2004/0193217 A1 | 9/2004 | Lubbers et al. |
| 2006/0058732 A1 | 3/2006 | Harp |
| 2006/0079919 A1 | 4/2006 | Harp |
| 2006/0200153 A1 | 9/2006 | Harp |
| 2006/0200154 A1 | 9/2006 | Harp |
| 2006/0200155 A1 | 9/2006 | Harp |
| 2006/0206117 A1 | 9/2006 | Harp |
| 2008/0058820 A1 | 3/2008 | Harp |
| 2009/0234274 A1 | 9/2009 | Luloh et al. |
| 2009/0270895 A1 | 10/2009 | Churchill et al. |
| 2009/0270897 A1 | 10/2009 | Adams et al. |
| 2009/0270898 A1 | 10/2009 | Chin et al. |
| 2010/0049320 A1 | 2/2010 | Lubbers et al. |
| 2010/0312102 A1 | 12/2010 | Barnes et al. |
| 2011/0034943 A1 | 2/2011 | Churchill et al. |
| 2012/0116404 A1 | 5/2012 | Harp |
| 2012/0123462 A1 | 5/2012 | Lee |
| 2013/0018404 A1 | 1/2013 | Berberich |
| 2013/0158579 A1 | 6/2013 | Underwood et al. |
| 2013/0158580 A1 | 6/2013 | Underwood et al. |
| 2013/0158581 A1 | 6/2013 | Underwood et al. |
| 2013/0158582 A1 | 6/2013 | Underwood et al. |
| 2013/0158583 A1 | 6/2013 | Underwood et al. |
| 2013/0158584 A1 | 6/2013 | Underwood et al. |
| 2013/0331842 A1 | 12/2013 | Harp |
| 2014/0039523 A1 | 2/2014 | Austen |
| 2017/0049468 A1 | 2/2017 | Mautner et al. |

OTHER PUBLICATIONS

Written Opinion of the International Searching Authority for International Application No. PCT/US2015/027909, dated Aug. 3, 2015.
Extended European Search Report for European Application No. 15786588.2, dated Nov. 23, 2017.

SYSTEMS AND METHODS FOR TISSUE TREATMENT

CROSS REFERENCE TO RELATED APPLICATIONS

This application is a continuation of U.S. application Ser. No. 15/307,070, filed Oct. 27, 2016, which is the national stage of PCT/US2015/027909, filed Apr. 28, 2015, which claims priority to U.S. Provisional Application No. 61/985,012, filed Apr. 28, 2014, all of which are hereby incorporated by reference.

BACKGROUND

Overuse of musculoskeletal tissues, such as tendons, plantar fascia, etc., can result in degenerative tissue (e.g., tendinopathy, plantar fasciitis, etc.) leading to pain and disability.

The damaged tissue is typically treated with NSAIDS, corticosteroid injections, physical therapy, platelet rich plasma injections, percutaneous needle tenotomy, or open surgery. Percutaneous needle tenotomy (PNT) is a minimally invasive procedure in which a needle is introduced to break up the tissue (e.g., scarred tissue, degenerated tissue, pathological tissue, etc.). This micro trauma induces an acute injury thus restarting the healing cycle and helping new, healthy tissue to form. However, a physician typically performs a PNT with manual repeated fenestration (see, e.g., http://www.aapmr.org/education/Ultrasound/Tendinopathy/Documents/Finnoff-PRP.PDF, and http://www.mayoclinic.org/medical-professionals/clinical-updates/physical-medicine-rehabilitation/treating-recalcitrant-tendinopathy) of the tissue with a needle or similar apparatus. Additionally, the procedure is typically performed in a surgical operating room setting thereby resulting in extensive costs.

SUMMARY

Thus, there is a need for accurate, efficient, and economic systems and methods for performing a percutaneous needle tenotomy.

The disclosure relates to systems and methods for treating a tissue site. In some embodiments, the system may include a body having a length and configured to receive a portion of the instrument guide member having an exposed end and/or an instrument; and an actuator member disposed within the body and configured to linearly oscillate the instrument within the instrument guide member a fixed distance past the exposed end.

In some embodiments, the system may include a body having a length and configured to receive a portion of the instrument guide member having an exposed end and/or an instrument; and an actuator member disposed within the body and configured to linearly oscillate the instrument within the instrument guide member a fixed distance past the exposed end without causing the instrument guide member to move.

In some embodiments, the system may include an instrument assembly including an instrument guide member having an exposed end and an instrument a body having a length and including a receiving member configured to removably attach the instrument assembly to the body; and an actuator member disposed within the body and configured to linearly oscillate the instrument within the instrument guide member a fixed distance past the exposed end without causing the instrument guide member to move.

In some embodiments, the system may include a body having a length and configured to receive a portion of the instrument guide member having an exposed end and/or an instrument; and an actuator member disposed within the body and configured to linearly oscillate the instrument between forward and backward positions within the instrument guide member. In the forward position, the instrument may be disposed a fixed distance past the exposed end. In the backward position, the instrument may be disposed within the instrument guide member and/or the body.

Additional advantages of the disclosure will be set forth in part in the description which follows, and in part will be obvious from the description, or may be learned by practice of the disclosure. The advantages of the disclosure will be realized and attained by means of the elements and combinations particularly pointed out in the appended claims. It is to be understood that both the foregoing general description and the following detailed description are exemplary and explanatory only and are not restrictive of the disclosure, as claimed.

BRIEF DESCRIPTION OF THE DRAWINGS

The disclosure can be better understood with the reference to the following drawings and description. The components in the figures are not necessarily to scale, emphasis being placed upon illustrating the principles of the disclosure.

DETAILED DESCRIPTION

Figure 1:
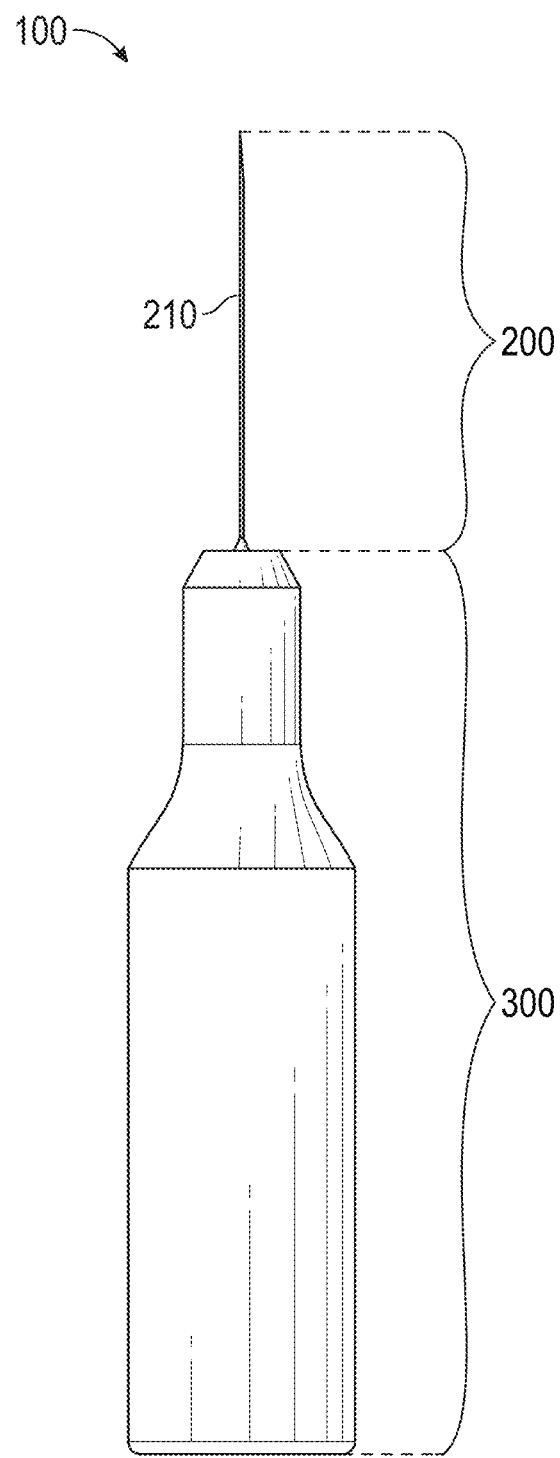
FIG. 1 shows a system according to some embodiments.

In the following description, numerous specific details are set forth such as examples of specific components, devices, methods, etc., in order to provide a thorough understanding of embodiments of the disclosure. It will be apparent, however, to one skilled in the art that these specific details need not be employed to practice embodiments of the disclosure. In other instances, well-known materials or methods have not been described in detail in order to avoid unnecessarily obscuring embodiments of the disclosure. While the disclosure is susceptible to various modifications and alternative forms, specific embodiments thereof are shown by way of example in the drawings and will herein be described in detail. It should be understood, however, that there is no intent to limit the disclosure to the particular forms disclosed, but on the contrary, the disclosure is to cover all modifications.

The methods and systems according to embodiments may be configured to mechanically treat targeted musculoskeletal tissue. For example, the methods and systems can be used to fenestrate and/or release of scar and/or degenerated tissue in tendon, ligament, muscle, and fascia; disrupt and/or remove soft tissue calcification; debride soft tissue, cartilage, or bone; among others; or a combination thereof. The systems can be designed to be an ergonomic and lightweight so that the system can be easily maneuvered by the clinician. The systems also can enable clinicians to perform procedures under local anesthesia in their office rather than the operating room, and therefore the systems can be a low-cost solution. The methods and systems can be used with medical imaging, for example, under ultrasound guidance. Therefore, the methods and systems can increase patient comfort while empowering clinicians by simplifying interventions for musculoskeletal disorders.

The methods and systems are discussed with respect to treating a targeted area/site. Treating may include but is not limited to puncturing, fragmenting, cutting, lysing, debriding, among others, or any combination thereof. A targeted area may be any area of musculoskeletal tissue. For example, a targeted area/site may include but is not limited to tissue (e.g., tendons) in shoulders, elbows, knee, ankle, foot, among others, or any combination thereof.

Figure 2:
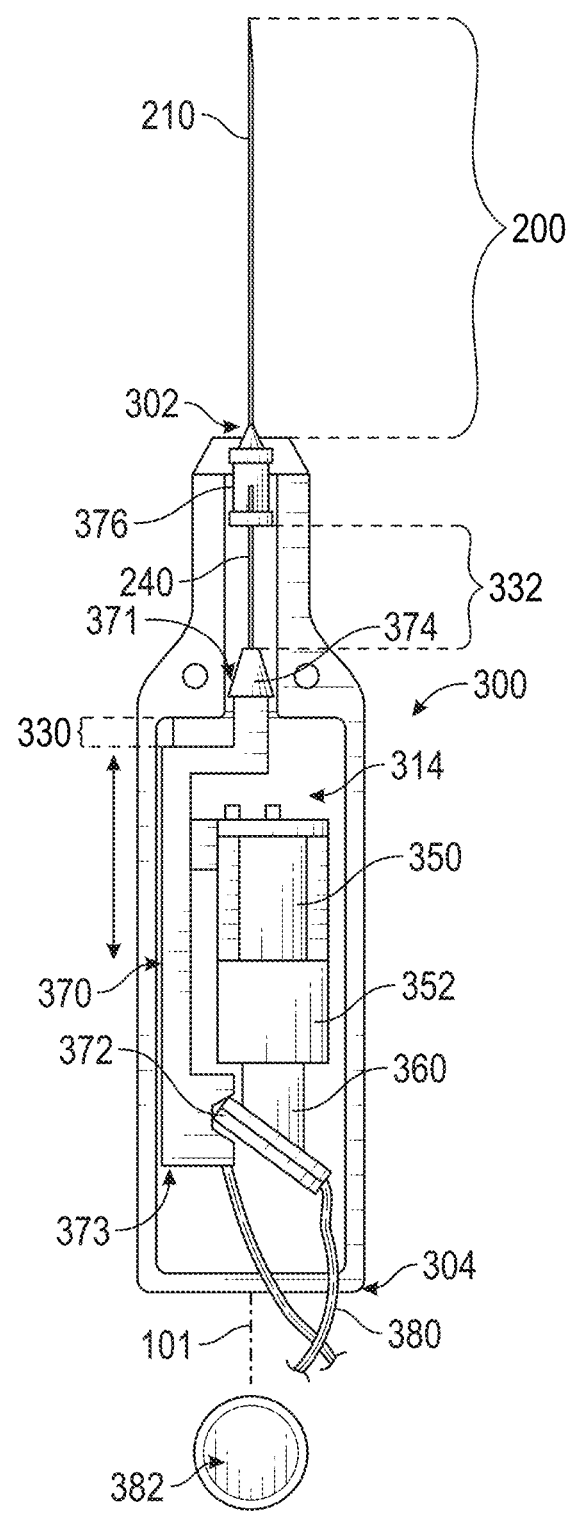
FIG. 2 shows a partial exposed view of a system according to some embodiments.
Figure 3:
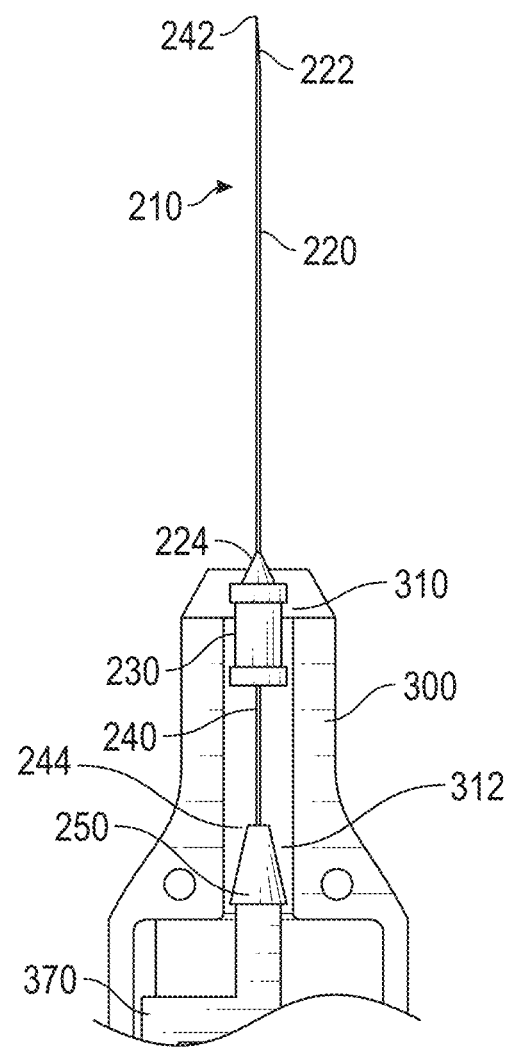
FIG. 3 shows an enlarged view of the system of FIG. 2.
Figure 4:
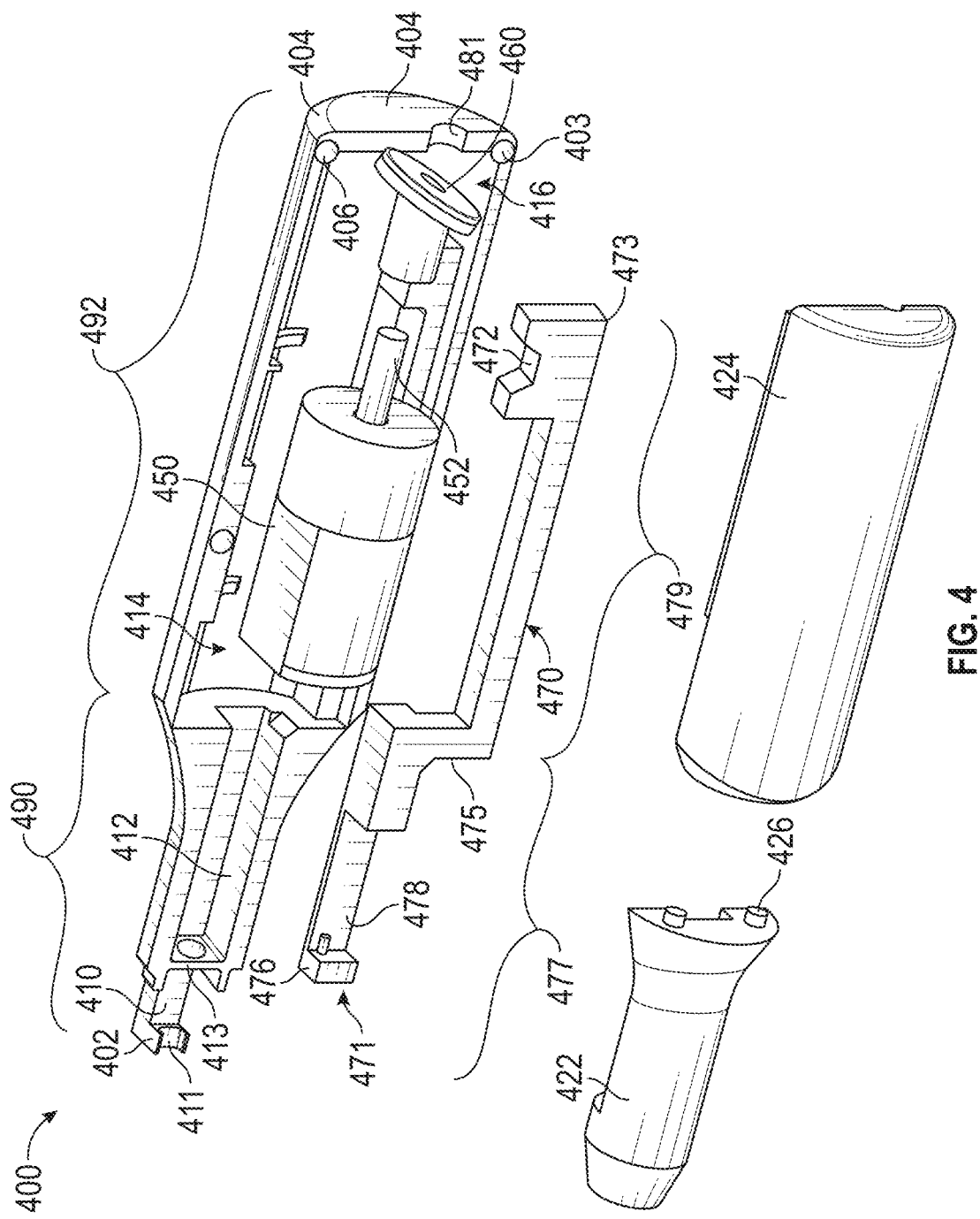
FIG. 4 shows a partial, exploded view of a system according to embodiments.

FIG. 1 shows a system 100 configured to treat tissue according to some embodiments. As shown in FIG. 1, the system 100 may include an instrument assembly 200 and a (device) body 300. FIGS. 2 and 3 show partial exposed views of the system 100. FIG. 4 shows a partial, exploded view of a (device) body according to embodiments.

In some embodiments, the instrument assembly 200 may be configured to be removably attached to the body 300. The instrument assembly 200 may include an instrument guide 210 configured to provide access to a targeted tissue area and an instrument 240. The instrument guide 210 may be configured to provide a stabilizing path to the targeted tissue area for an instrument when attached to the body 300. The instrument guide 210 may be configured to be stationary when attached to the body 300 and the instrument 240 may be configured to linearly move within the instrument guide 210 to one or more fixed distances. In this way, the instrument 240 can be moved without moving the instrument guide 210. Thus, the instrument guide 210 can control the disruption to the targeted area by preventing the disruption of the surrounding tissue by the instrument guide 210 and/or the instrument 240.

In some embodiments, the instrument guide 210 may include an instrument guide member 220 having a first (exposed) end 222, a second end 224, and a length there between. The length of the instrument guide member 220 may vary and for example, may depend on the instrument to be guided, the target area to be treated, among others, or a combination thereof.

In some embodiments, the instrument guide member 220 may have an elongated tubular shape, for example, such as a cannula. In some embodiments, the instrument guide member 220 may have a circular cross-section. In other embodiments, the instrument guide member 220 may have a different cross-section, such as rectangular or triangular.

In some embodiments, the instrument guide member 220 may be configured to directly penetrate tissue to access the target area. In some embodiments, the instrument guide member 220 may include a tip configured to penetrate tissue. In some embodiments, the end 22 may include a sharp tip. The tip may include but is not limited to a pointed tip, tapered tip, blunt tip, as well as others. In other embodiments, the end 222 may have a different tip.

In some embodiments, the instrument 240 may include a first end 242, a second end 244, and a length there between. The length of the instrument 240 may vary and for example, may depend on the length of the instrument guide member 220, the target area to be treated, among others, or a combination thereof. In some embodiments, the instrument 240 may be the same, shorter, and or longer than the instrument guide 210.

In some embodiments, the instrument 240 may be any instrument configured to treat tissue. The instrument 240 may include but is not limited to an instrument configured to disrupt, debride, decorticate, fragment among others, or a combination thereof. The instrument may be configured to puncture or pierce tissue. For example, the instrument 240 may include one or more hollow and/or solid needles. In some embodiments, the needles may include on the first end 242 and/or along a portion of the length a sharp point, one-sided serrated edge, a blunt point, a ball shape at the end (e.g., a mace), textured and/or granulated surface, a tapered point, a flat edge/end, a pointed tip, a bur tip, among others, or a combination thereof.

In some embodiments, the instrument assembly 200 may include one or more attachment members configured to removably attach the instrument assembly 200 to the body 300. In some embodiments, the instrument guide 210 and/or the instrument 240 may include an attachment member. The instrument guide 210 and/or the instrument 240 may be configured to be separately removable from the body 300 and/or the instrument assembly 200. For example, as shown in FIG. 3, the instrument guide 210 may include an attachment member 230 disposed at the end 224 and the instrument 240 may include an attachment member 250 disposed at the end 244. The attachment members 230 and 250 may be the same or different. For example, the attachment members 230 and/or 250 may include a hook, a plug, a magnet, a luer lock, among others, or a combination thereof. In some embodiments, the attachment members 230 and/or 250 may include an opening. For example, as shown in FIG. 3, the attachment member 230 may include an opening through which the instrument 240 may linearly move.

In some embodiments, the instrument assembly 200 may include an attachment member configured to removably attach the instrument assembly 200 (e.g., at least the instrument guide and the instrument) to the body 300. For example, the instrument assembly 200 may include a housing in which the instrument guide 210 and/or the instrument 210 may be included so that the instrument assembly 200 is self-contained and encased. In this example, at least the housing may include an attachment member configured to removably attach the instrument assembly to the body. In some embodiments, the instrument guide 210 and/or the instrument 240 may additionally be configured to be separately removable from the instrument assembly 200. For example, the instrument guide 210 and/or the instrument 240 may be configured to be removed from the housing and/or each other. By way of example, the instrument guide 210 may be configured to be removable from the instrument assembly 200, the instrument 240 and/or body 300 so that the instrument guide 240 can remain in the patient after being used. In this example, the instrument guide 240 may be configured to deliver therapeutic agent(s) to the site.

In some embodiments, the housing and/or the instrument guide may include a mechanism configured to receive a syringe to deliver a therapeutic agent. For example, the mechanism may be a luer lock mechanism that is configured to attach a syringe to the instrument guide and/or housing.

The body 300 may include a first end 302, a second end 304, and a length there between. The body 300 may also include a longitudinal axis 101 that is parallel to its length. In some embodiments, the body 300 may include one or more inner compartments disposed along the length for one or more components of the system 100.

As shown in FIG. 3, in some embodiments, the system 100 may include an actuator 350 disposed in the body 300 and configured to cause the instrument 240 to linearly oscillate within the guide member 220 so that the instrument 240 extends past the (exposed) end 222 one or more fixed distances. The fixed distance can correspond to the maximum length that the instrument 200 is exposed past the instrument guide (e.g., the maximum distance between the end 242 of the instrument and end 22 of the instrument guide). In some embodiments, the actuator 350 may be a motor.

In some embodiments, the system 100 may include a rotatable drive shaft 352 disposed adjacent to the actuator 350. In some embodiments, the body 300 may include an inner compartment 314 in which the actuator 350 and the rotatable drive shaft 352 may be fixedly disposed.

In some embodiments, the system 100 may include at least one rotatable member 360 disposed in the body 300 on the rotatable drive shaft 352 (not visible; see FIG. 4) of the actuator 350. In some embodiments, the rotatable member 360 may be a barrel cam. As shown in FIG. 2, the rotatable member 360 may be a radial/disc cam tilted at a defined angle with respect to the actuator. In some embodiments, the rotatable member 360 may be another type of cam. For example, the rotatable member 360 may be a curved disc, cylindrical cam, a drum cam, a globoidal cam, among others, or a combination thereof. In other embodiments, the at least one rotatable member 360 may be one or more gears.

In some embodiments, the system 100 may include a linear oscillating member 370 disposed in the body 300 and configured to move linearly with respect to the length of the body 300. In some embodiments, the linear oscillating member 370 may be an elongated shaft. In some embodiments, the linear oscillating member 370 may include a first end 371, a second end 373, and a length there between. In some embodiments, the linear oscillating member 370 may be disposed within the body 300 so that it extends from the rotatable member 360 between the instrument 240 and/or the instrument guide 220.

In some embodiments, the linear oscillating member 370 may include one or more receiving members configured to receive the rotatable member 360. As shown in the FIG. 3, the linear oscillating member 370 may include a receiving member 372 for the rotatable member 360. As shown in FIG. 2, the receiving member 372 may be disposed near the end 373. In some embodiments, the receiving member 372 may be a slot and/or aperture configured to receive the rotatable member 360 and in which the rotatable member 360 may rotate. When the rotatable member 360 is disposed in the receiving member 372, the rotatable member 360 may be configured to transform the rotary motion of the actuator 350 via the rotatable member 360 to cause the instrument 240 to linearly oscillate.

In some embodiments, in operation, the actuator 350 may be configured to rotate 360° (e.g., make full revolutions) to cause the linear oscillating member 370 to move in a linear, oscillating manner. In other embodiments, in operation, the actuator 350 may be configured to rotate a partial revolution (e.g., rotate less than rotate 360°) and reverse rotation direction when the actuator 350 reaches the end of the partial revolution in that direction to cause the linear oscillating member 370 to move in a linear, oscillating manner via the linear oscillating member 370.

In some embodiments, the body 300 may include one or more receiving members for the instrument assembly 200. In some embodiments, the body 300 may include one or one receiving members disposed about the first end 302. For example, the body 300 may include a self-contained opening and/or slot configured to receive one or more attachment members of the instrument assembly 200. In this example, the instrument assembly 200 may be encased and may include one or more attachment members on the bottom (e.g., the side opposite the exposed end of the instrument guide 220). For example, the body may include a first receiving member 310 and a second receiving member 312 for respectively receiving attachment members 230 and 250 of the instrument assembly 200.

In some embodiments, the one or more receiving members for the instrument assembly 200 may be disposed within the one or more inner compartments of the body 300. In some embodiments, the linear oscillating member 370 may include a receiving member 374 configured to receive the tool 240. In some embodiments, the receiving member 374 may be disposed about the end 371. In some embodiments, the receiving member 374 may be disposed within the linear oscillating member (see FIG. 5). In some embodiments, the body 300 may include a receiving member 376 for the instrument guide 210.

In some embodiments, the body 300 may be ergonomically configured to fit within the user's hand. In some embodiments, the body 300 may include contoured surfaces to facilitate grasping by the user. In some embodiments, the body 300 may include a trigger member configured to directly or indirectly cause the actuating member 350 to be activated (i.e., powered). For example, the trigger member may be a button or a mechanical switch configured to directly activate the actuating member 350. In some embodiments, the button or mechanical switch may be disposed on the body 300 to ergonomically align with a user's thumb or other fingers when the body 300 is held in the user's hand.

In some embodiments, the body 300 may include additional and/or alternative buttons or switches. For example, the body may include a dial or press a button configured to adjust the fixed distance of the instrument 240. In another example, the body 300 may include a dial or press a button configured to adjust the speed of the linear oscillation of the instrument 240. In a further example, the body 300 may include a button to control the position of the instrument with respect to the instrument guide (e.g., when the power to the actuator is stopped). In this example, the button may be configured to cause the actuator to move so that the instrument is retracted within the instrument guide. In some embodiments, the actuator 350 may cause the instrument 240 to retract within the instrument guide member 220 when the actuating member 350 is deactivated.

In some embodiments, the trigger member may be a foot-operated switch that is either electrically connected to the body 300 or wirelessly coupled to the body 300 (e.g., via blue-tooth communication technology). In some embodiments, a computer that is either electrically connected to the body 300 or wirelessly coupled to the body 300 may be configured to control and/or activate the actuating member 350. In some embodiments, the foot-operated switch and/or computer may control one or more output functions (e.g., speed, fixed distance, or the like) in addition to and/or in the alternative to the controls being located on the body 300.

In some embodiments, the system 100 may include a power source 380. The power source 380 may be any source configured to provide electrical power to the body 300. For example, the power source 380 may be configured to directly or indirectly deliver power to the actuator 350. In some embodiments, the power source 380 may be a battery 382 disposed within an inner compartment of the body 300. The battery 280 may be rechargeable and/or replaceable. In some embodiments, the power source 280 may be an external source, such as a power supply or wall socket, or a combination thereof.

In some embodiments, as shown in FIG. 3, the actuator 350 may be disposed between the rotatable member 360 and the instrument 240. The linear oscillating member 370 may be disposed adjacent to the actuator 350 so that the linear oscillating member 370 extends along the length of actuator from about the rotatable member 360 and the instrument assembly 200. In this way, the body 300 may have a more compact and narrower design.

In operation, the actuator 350 may be configured to control, the instrument 240 so that it linearly oscillates a fixed distance (i.e., the length of the exposed instrument 200 past the instrument guide member 220 at end of oscillation (e.g., the maximum distance between the end 242 of the instrument 240 and the end 222 of the instrument guide 210)). In this way, the instrument can repeatedly puncture and/or fenestrate and/or pierce the target tissue. In some embodiments, the fixed distance may be based on the angle and/or rotation of the rotatable member; the distance between the instrument guide, the instrument, and/or body (e.g., linear oscillating member; see area 332); and/or the distance between the linear oscillating member and the inner compartment (e.g., area 330).

In some embodiments, the system 100 may be configured to oscillate one or more fixed distances. For example, the fixed distance may be set by the user. The body 300 and/or instrument assembly 200 may be configured to set one or more fixed distances for which the instrument 240 may repeatedly move. For example, the fixed distance may correspond to the distance between the instrument 240 and instrument guide 210 selected by the user on the instrument assembly 200; the angle and/rotation of the rotatable member 370; among others; or a combination thereof.

In operation, the actuator 350 (e.g., via the linear oscillating member 350) can cause the instrument 240 to repeatedly move linearly between a forward position (away from the body 300) and a backward position (towards the body 300) along the longitudinal axis 101 of the body with respect to the instrument guide member 220 and/or body 300. In the forward position, the instrument 240 may extend a fixed distance beyond the instrument guide member 220 and therefore a portion of the instrument 240 corresponding to the fixed distance may be exposed to treat the tissue. In the backward position, the instrument 240 may be disposed within the instrument guide member 230, instrument assembly 200, and/or a self-contained portion of the body 300. In some embodiments, the instrument 240 may be configured to be disposed in a resting position. In this way, although the instrument assembly 200 may be exposed to tissue and bodily fluid, the components of the body 300 may remain sterile.

To activate the actuator 350, a user may press the triggering member (e.g., power button) to cause the actuator 350 to rotate thereby causing the rotatable member 360 to rotate (via the rotatable drive shaft 352). The rotatable member 360 and actuator 350 may be disposed so that the rotation motion is about the longitudinal axis 101 of the body 300. The rotation motion of the rotatable member 360 can then cause the linear oscillating member 370 to linearly oscillate along the central axis 301 (e.g., repeatedly move forward/backward with respect the length of the device). The linear oscillating member 370 can then transfer the linear motion to the instrument 240. The instrument 240 can be configured to linearly oscillate within the stationary instrument guide member 220. In some embodiments, the backward and forward positions of the instrument 240 with respect to the instrument guide member may be configured to depend on the angle of the portion of the rotatable member 360 that is disposed within the linear oscillating member 370.

In some embodiments, the system 100 may include a controller (e.g., a microprocessor and/or any type of processor) configured to control the speed and/or revolutions of the actuator 350, a position of the instrument 240 with respect to the instrument guide member 220, among others, or a combination thereof. For example, the actuator 350 may be configured to cause revolutions at different speeds, which can be selectable by the user. In another example, the controller may be configured to control the position of the instrument 240 with respect to the instrument guide member 200 when the power to the actuator 350 is discontinued (e.g., by powering off or by selecting a button). For example, the controller may case the instrument 240 to move to the resting position.

FIG. 4 shows a partial exploded view of a body 400. FIG. 4 does not show an instrument assembly. It is understood that the embodiments of the instrument assembly 200 described with respect to FIGS. 1-3 may also be used with the system shown in and described with respect to FIG. 4. It is understood that the embodiments of the body, actuator, rotatable member, and linear oscillating member, described with respect to FIGS. 1-3 may also apply to the body, actuator, rotatable drive shaft, rotatable member, and linear oscillating member described with respect to FIG. 4, and vice versa. The body, actuator, rotatable drive shaft, rotatable member, and linear oscillating member described with respect to FIG. 4 may be similar with some respects to the body, actuator, rotatable drive shaft, rotatable member, and linear oscillating member described with respect to FIGS. 1-3.

Like the body 300, the body 400 may have a first end 402, a second end 404, and a length there between. In some embodiments, the body 400 may include one or more sections. In some embodiments, the body 400 may include a first section 490 and a second section 492. In other embodiments, the body 400 may include more or less sections.

Like the system 100, the system shown in FIG. 4 may include an actuator 450 including a rotatable shaft 452, a rotatable member 460, and a linear oscillating member 470. The actuator 450 may be configured to rotatably drive the rotatable member 460, which in turn causes the linear oscillating member 470 to linearly oscillate (i.e., repeatedly move in a backward and forward manner).

As shown in FIG. 4, the linear oscillating member 470 may include a first end 471, a second end 473, and a length there between. In some embodiments, the linear oscillating member 470 may include one or more sections. In some embodiments, the linear oscillating member 470 may include a first section 477 and a second section 479. In some embodiments, the first section 477 may include a portion of the linear oscillating member 470, for example, from first end 471 to intermediary area 475, and the second section 479 may include a portion of the linear oscillating member 470, from the intermediary area 475 to the second end 475. In some embodiments, like the oscillating member 370, the oscillating member 470 may include a receiving member 472 configured to receive the rotatable member 460. The receiving member 472 may be configured so that the rotatable member 460 may be rotate within the receiving member 472.

In other embodiments, the body 400 may include one or more inner compartments configured to receive the actuator 450, the rotatable shaft 452, a rotatable member 460, and the linear oscillating member 470. In some embodiments, the body 400 may include a first inner compartment 412 to receive the instrument assembly 200 and/or a portion of the linear oscillating member 470; a second inner compartment 414 to receive a portion of the linear oscillating member 470, the actuator 450, and/or the rotatable member 460; and a third inner compartment 416 to receive a power source. In some embodiments, the inner compartment 412 may be disposed in the first section 490 and the inner compartments 414 and 410 may be disposed in the second section 492.

In some embodiments, the actuator 450 and the second section 479 may be disposed in the inner compartment 414 so that the actuator 450 is disposed within the length of the second section 479.

In some embodiments, the linear oscillating member 470, the actuator 450, and the rotatable member 416 may be fixedly disposed within the inner compartments. In some embodiments, the instrument assembly 200 and/or the power source (not shown; see FIG. 2) may be fixedly disposed within the inner compartments. In some embodiments, the instrument assembly 200 and/or the power source may be removably disposed within the inner compartments. For example, the body 400 may be a reusable device and the instrument assembly 200 may be replaced for each use. In another example, the power source may be a replaceable battery. In these examples, the inner compartments that are configured to be accessible to replace the instrument assembly 200 and/or power source may be self-contained so as not to contaminate the other inner compartments.

In some embodiments, the first section 490 may be configured to communicate with the instrument assembly 200. For example, in some embodiments, the first section 490 may be configured to directly and/or indirectly receive the instrument assembly 200. By way of example, the first section 490 and/or the linear oscillating member 470 may be configured to receive the instrument assembly 200. By way of example, the body 400 may include a receiving member 410 (e.g., an inner compartment) to receive an instrument guide 210. When the instrument guide 210 is disposed in the receiving member 410, the receiving member 410 may be configured to fixedly dispose the instrument guide 210 so that it is stationary while the instrument 240 is moving.

In some embodiments, the linear oscillating member 470 may include a receiving member 478 configured to receive the instrument 240. When the instrument 240 is disposed in the receiving member 478, the instrument 240 may move with the linear oscillating member 470. The linear oscillating member 470 may include an opening and/or channel 476 through which an instrument may be disposed so that it can extend through the body 400.

The body 400 may be configured so that the instrument assembly 200, instrument guide 210 and/or the instrument 240 may be removed after use. The body 400 may also include an opening and/or aperture 411 through which the instrument guide 210 and/or instrument 240 may extend through the body.

In some embodiments, the embodiments, the receiving members 410 and/or 478 may be omitted. For example, the opening and/or aperture 411 may be configured to receive and communicate with an encased instrument assembly 200 so that the linear oscillating member 470 can cause the instrument 210 to linearly oscillate.

In some embodiments, the body may include one or more cases configured to cover the one or more inner compartments. In some embodiments, the one or more cases may be configured to be removably attached. As shown in FIG. 4, the body 400 may include cases 422 and 424. For example, the case 422 may be configured to be fixed to the body 400 to cover the first section 490 and the case 424 may be configured to be removable attached to cover the second section 492. The case 422 may include one or more attachment members 426 configured to attach the case 422 to the case 424 and the case 424 may include complimentary receiving members. In some embodiments, the body 400 may include complementary receiving members 406 configured to receive the case 422 and/or the case 424. The attachment members, for example, may be a protruding member and the receiving members may be holes. In other embodiments, the one or more attachment members may be different. For example, the one or more attachment members may be magnetic, hook, luer lock, among others. In other embodiments, the body may include one case that may be configured to be fixed and not removable by the user.

Figure 5:
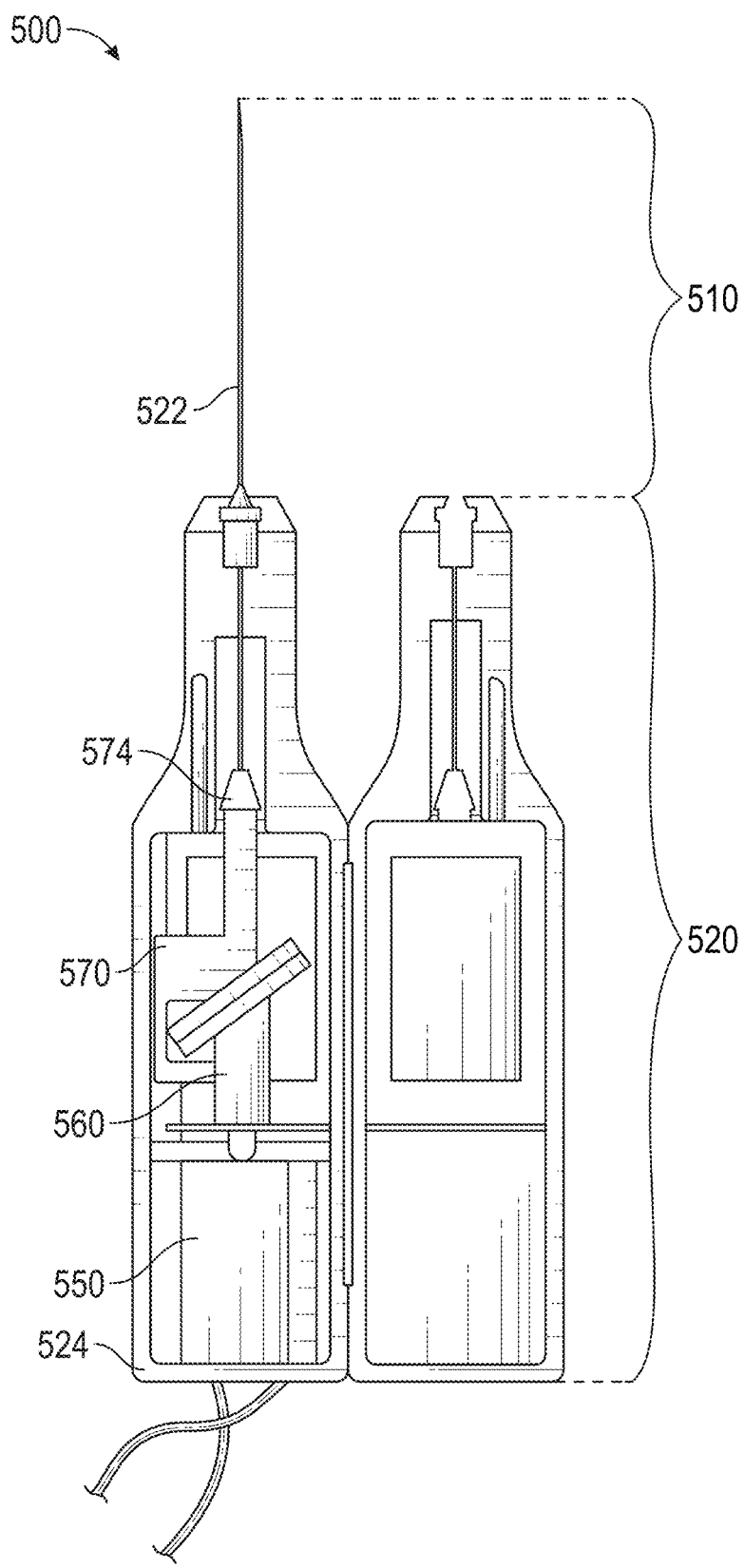
FIG. 5 shows a system according to embodiments.

It will also be understood that the configurations of body, actuator, rotatable member, and linear oscillating member, shown in FIGS. 1-4 are not limited to those shown in the figures and may include other configurations. For example, these components disposed in a different configuration, as shown in FIG. 5. FIG. 5 shows a system 500 according to some embodiments. As shown in FIG. 5, a system 500 may include an instrument assembly 510 and a body 520. Like the body 300, the body 500 has a first end 522, a second end 524, and a length there between. The body 300 may include an actuator 550, a rotatable member 560, and a linear oscillating member 570. The system 500 is similar to the system 100 but for the locations of the actuator 550, the rotatable member 560, and the linear oscillating member 570. As shown in FIG. 5, the rotatable member 360 may be disposed between the instrument assembly 200 and the actuator 550. In this example, the linear oscillating member 570 can have a shorter length because the actuator 550 can be disposed not along the length. The system 500 may operate in a similar fashion as the system shown and described with respect to FIGS. 1-4.

In other embodiments, the actuator may include a drive shaft that is configured to move linearly (i.e., oscillates in a forward/rearward directions or axially). In this example, the rotatable drive shaft, rotatable member/or the linear oscillating member may be omitted and/or replaced with different components.

In some embodiments, one or more components of the system may be made of echogenic material. In this way, the one or more components may be visible under medical imaging.

In some embodiments, the system may be used in a method of treating a tissue site. For example, the system may be used to debride, fragment, or lyse tissue in a controlled manner so as to induce a controlled injury. The system can be used in an office or ambulatory surgical suite under external or internal medical imaging guidance, such as ultrasound, fluoroscopy, and/or other internal imaging visualization modalities.

In some embodiments, the method of treating a tissue site with the system may include attaching the instrument assembly to the body. For example, a case may be removed to access a first section of the body to attach the instrument guide and instrument. In other example, a housing including the instrument assembly may be attached to the body without having to remove a case. Next, the instrument guide may be inserted into a patient to the targeted tissue site, for example, using medical imaging guidance. After the instrument guide is in place, the clinician may activate the actuator (e.g., by pressing the triggering member) to cause the instrument to repeatedly move linearly oscillate. In this way, the actuator causes instrument to automatically and repeatedly move linearly into the target site past the instrument guide a fixed distance. The repeated motion of the instrument can cause debridement/lysing/fragmentation of the tissue to thereby cause localized disruption/damage to the targeted tissue. In some embodiments, the clinician may select the fixed distance and/or speed before and/or after the insertion of the instrument guide. After the desired debridement/fragmentation is achieved, the clinician may stop the activation of the actuator. In some embodiments, the body and/or a part of the instrument housing may be removed while leaving the instrument guide in the target site. In this way, the instrument guide may be used to access the target site, for example, to deliver a therapeutic agent. Because at least most of the body is self-contained, the body can be reused with a new instrument assembly for another patient.

In some embodiments, one or more components of the system may be sterilized. In some embodiments, one or more parts of the system may be reused. For example, the body may be configured to be reused. In some embodiments, one or more parts of the system may be disposable. In further embodiments, the system may be a single, use device. For example, the instrument assembly 200 may be configured to be a single, use device.

In some embodiments, the system may be part of a kit. In some embodiments, the kit may include the instrument assembly and/or the body. In some embodiments, the kit may include one or more instrument assemblies. For example, the kit may include a plurality of different kinds and/or sizes of instruments, corresponding instrument guides, or a combination thereof.

While the disclosure has been described in detail with reference to exemplary embodiments, those skilled in the art will appreciate that various modifications and substitutions can be made thereto without departing from the spirit and scope of the disclosure as set forth in the appended claims. For example, elements and/or features of different exemplary embodiments may be combined with each other and/or substituted for each other within the scope of this disclosure and appended claims.

That which is claimed is:

1. A method for treating a targeted tissue site, the method comprising:
    providing a tissue treatment device comprising a body including first and second receiving members configured to receive and releasably retain a self-contained instrument assembly thereto, and an actuator disposed within the body and configured to linearly oscillate the instrument within the instrument guide member;
    attaching a self-contained instrument assembly to the body of the tissue treatment device, the instrument assembly including both an instrument guide member and an instrument at least partially disposed within the instrument guide member, wherein the instrument assembly is received and releasably retained to the body by way of engagement between the first receiving member of the body and a corresponding attachment member of the instrument assembly and engagement between the second receiving member located at a distal portion of the body and configured to operably couple with the instrument;
    accessing, via the instrument guide member of the instrument assembly, a targeted tissue site; and
    activating the actuator to cause the instrument to linearly oscillate within the instrument guide member a fixed distance past an exposed end of the instrument guide member to thereby treat tissue at the targeted tissue site.

2. The method of claim 1, wherein the body includes one or more inner compartments, at least one of the one or more inner compartments being self-contained.

3. The method of claim 1, wherein the tissue treatment device further comprises:
    a rotatable member disposed on a shaft of the actuator, the shaft and the rotatable member being configured to rotate about a longitudinal axis of the body; and
    a linear oscillating member including a first receiving member configured to receive a portion of the rotatable member;
    wherein the rotatable member is configured to transform rotations of the shaft via the linear oscillating member to cause the instrument to linearly oscillate.

4. The method of claim 3, wherein the actuator is disposed between the rotatable member and the instrument.

5. The method of claim 3, wherein the linear oscillating member includes a second receiving member configured to receive and releasably retain a portion of the instrument.

6. The method of claim 1, wherein the instrument guide member is configured to be stationary with respect to the body of the tissue treatment device.

7. The method of claim 1, wherein the instrument comprises a first end for treating the tissue at the targeted tissue site based upon repeated linear motion of the first end of the instrument a fixed distance past the exposed end of the instrument guide member and into repeated contact with the tissue.

8. The method of claim 7, further comprising repeatedly contacting the tissue with the first end of the instrument to cause localized disruption and/or damage to the tissue at the targeted tissue site.

9. The method of claim 8, wherein causing localized disruption and/or damage to the tissue induces a controlled injury for promoting formation of healthy tissue at the targeted tissue site.

10. The method of claim 8, wherein the first end of the instrument is configured to cause at least one of disruption, debridement, fragmentation, puncturing, piercing, and a combination thereof, to the tissue at the targeted tissue site.

11. A method for treating a targeted tissue site, the method comprising:
    providing a tissue treatment system comprising a body including an actuator disposed within and a self-contained instrument assembly releasably coupled thereto, the instrument assembly includes both an instrument guide member and an instrument at least partially disposed within the instrument guide member and the body includes first and second receiving members configured to receive and releasably retain at least a portion of the instrument assembly to the body by way of engagement between the first receiving member of the body and a corresponding attachment member of the instrument assembly and the second receiving member located at a distal portion of the body and configured to operably couple with the instrument to thereby releasably retain both the instrument guide member and the instrument to the body;
    accessing, via the instrument guide member of the instrument assembly, a targeted tissue site;
    activating the actuator to linearly oscillate the instrument within the instrument guide member a fixed distance past an exposed end of the instrument guide member without causing the instrument guide member to move with respect to the body; and
    treating tissue at the targeted tissue site based on repeated linear oscillation of the instrument.

12. The method of claim 11, wherein the tissue treatment system further comprises:
    a rotatable member disposed on a shaft of the actuator, the shaft and the rotatable member being configured to rotate; and a linear oscillating member including a first receiving member configured to receive a portion of the rotatable member;

wherein the rotatable member is configured to transform rotations of the shaft via the linear oscillating member to cause the instrument to linearly oscillate.

13. The method of claim 12, wherein the actuator is disposed between the rotatable member and the instrument.

14. The method of claim 12, wherein:
the body includes one or more inner compartments, at least one of the one or more inner compartments being self-contained; and
the actuator, the rotatable member, and at least a portion of the linear oscillating member are disposed within one of the one or more inner compartments that are self-contained.

15. The method of claim 14, wherein the tissue treatment system further comprises a power source configured to activate the actuator, the power source being disposed in one of the one or more inner compartments.

16. The method of claim 11, wherein the actuator includes a shaft configured to rotate with respect to the body.

17. The method of claim 16, wherein the tissue treatment system further comprises:
a rotatable member disposed within the body, the rotatable member being configured to rotate with respect to the body upon rotation of the shaft; and
a linear oscillating member disposed within the body, the linear oscillating member being configured to linearly oscillate with respect to the body upon rotation of the rotatable member.

18. The method of claim 11, wherein the repeated linear oscillation of the instrument causes repeated linear motion of a first end of the instrument and into repeated contact with the tissue at the targeted tissue site to cause at least one of disruption, debridement, fragmentation, puncturing, piercing, and a combination thereof, to the tissue at the targeted tissue site for inducing a controlled injury.

19. The method of claim 18, wherein causing localized disruption and/or damage to the tissue induces a controlled injury for promoting formation of healthy tissue at the targeted tissue site.

20. The method of claim 18, wherein the instrument comprises a hollow needle or a solid needle.

* * * * *